(12) United States Patent
Gapihan

(10) Patent No.: US 6,328,197 B1
(45) Date of Patent: *Dec. 11, 2001

(54) AEROSOL DISPENSING CONTAINER AND METHOD FOR MANUFACTURING SAME

(75) Inventor: Jean Gapihan, Thourotte (FR)

(73) Assignee: United States Can Company, Lombard, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/032,721

(22) Filed: Feb. 28, 1998

(51) Int. Cl.$^7$ .............................. B23K 11/06; B23K 11/34
(52) U.S. Cl. ........................ 228/144; 228/184; 228/203; 219/64
(58) Field of Search ................................. 228/144, 184, 228/203; 219/61.12, 64, 78.14

(56) References Cited

U.S. PATENT DOCUMENTS

| 3,416,217 | 12/1968 | Walker | 29/403 |
|---|---|---|---|
| 5,364,012 | 11/1994 | Davis et al. | 228/184 |
| 5,433,099 | 7/1995 | Katsuhiro et al. | 72/347 |

FOREIGN PATENT DOCUMENTS

| 2-30382 | * 1/1990 | (JP) | 219/64 |
| WO 82/02697 A1 | * 8/1982 | (WO) | 219/64 |

* cited by examiner

*Primary Examiner*—Patrick Ryan
*Assistant Examiner*—Lynne Edmondson
(74) *Attorney, Agent, or Firm*—Polster, Lieder Woodruff & Lucchesi, L.C.

(57) ABSTRACT

A container body is made from a composite sheet having a metal layer which has at least one side covered by a corrosion-resistant layer, such as a layer of thermoplastic. The sheet is moved under one or more high-pressure water jets which remove a strip of the corrosion-resistant layer in the path of the water stream, leaving an exposed area. The composite sheet may be segmented as necessary to form blanks suitable for forming individual container bodies. Each blank is formed generally into a tube or cylinder so that the corrosion-resistant layer faces interiorly, and so that the exposed areas are respectively located at overlapping ends of the blank. The overlapping, exposed areas are then welded along a seam, forming a seal.

20 Claims, 4 Drawing Sheets

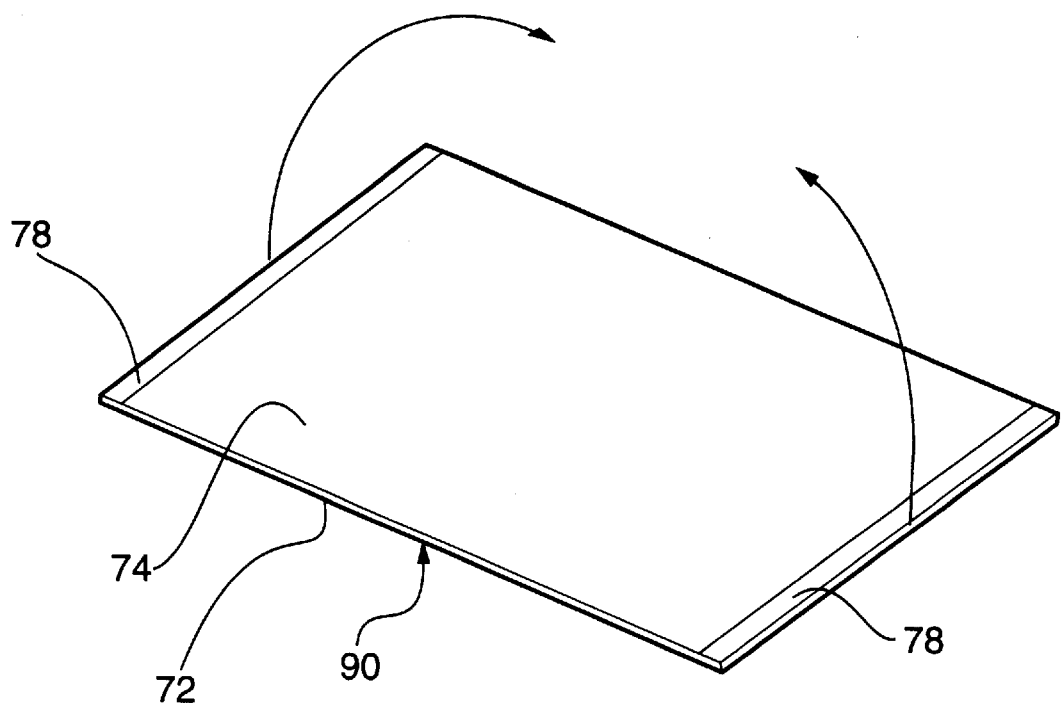
FIG. 5
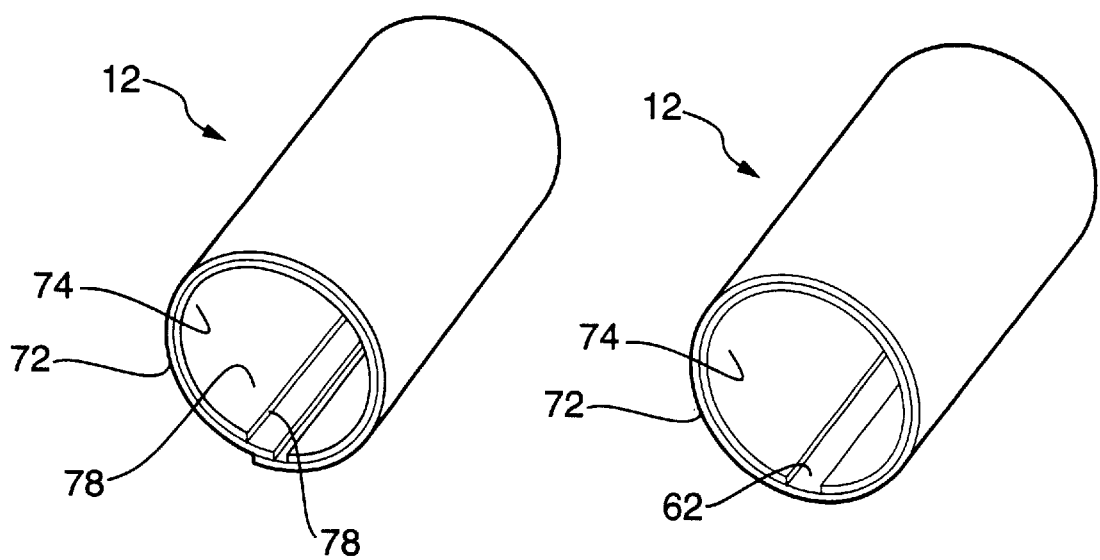
FIG. 6A  FIG. 6B

AEROSOL DISPENSING CONTAINER AND METHOD FOR MANUFACTURING SAME

FIELD OF THE INVENTION

The present invention relates to a dispensing container and more particularly, to an aerosol dispensing container formed by a welded metal sheet having a corrosion-resistant protective laminate.

BACKGROUND OF THE INVENTION

Known aerosol containers are made of a metal sheet which is wrapped into a cylindrical body so that overlapping edges may be welded into a seam. Shaped caps are fitted onto the ends in a sealed manner, and one of these seals is typically provided with a dispensing valve. Such a container is useful for containing a liquid product and a pressurized propellant.

It is desirable to use tinplated steel blanks to form cans in appropriate applications because such a material is inexpensive. Tinplated steel is suitable for a container so long as the contents do not corrode the tin and steel. Unfortunately, tinplated steel has been found unsuitable for many aerosol dispensing container applications because it tends to corrode when exposed to certain corrosive compounds found in certain applications such as saline solutions, hair mousse treatments, and dimethyl ether (DME) propellants. In an attempt to avoid corrosion, aerosol cans have typically been produced from aluminum or coated with thin organic coatings, which, although they exhibit good corrosion resistance, are also relatively expensive. However, constructing the body from tinplated steel requires some means of preventing exposure of the metal to the corrosive contents.

One known aerosol container prevents the product from contacting and corroding the metal container body using a collapsible bag for housing the product. The propellant, contained within the container body, exteriorly surrounds the bag and selectively compresses the bag to dispense the product in response to a release valve. Unfortunately, the presence of the bag requires additional components and assembly steps, which also increases costs.

Another means of preventing corrosion of the container body is to laminate or coat its interior and/or exterior surface with a corrosion-resistant layer. For example, certain varnishes, paints, inks or plastic laminates are suitable to protect a metal blank such as tinplated or tin-free steel from corrosion, so long as the corrosion-resistant layer is compatible with the product contents. Corrosion-resistant layers, such as coatings or laminates, if present at the overlapping weld site, however, introduce a foreign substance that can weaken the weld or prevent an effective weld from forming. Therefore, the overlapping area must be free from the coating or laminate material. Accordingly, it is known to apply the corrosion-resistant layer partially to the metal, leaving exposed portions or strip-shaped areas. For example, a lacquer coating or laminate can be applied to the metal blank in a striped pattern to leave exposed metal strips at the area to be overlapped and welded. After welding, a supplemental corrosion-resistant layer can be applied over the seam to prevent it from corroding. The process of applying a corrosion-resistant layer to only a predetermined portion of a sheet, however, can be expensive.

It is also known to coat or laminate the entire surface of the metal sheet, then remove portions of the corrosion-resistant layer to expose areas at the sites of metal to be welded. This is conventionally done by mechanical means, such as by sanding, grinding, milling, scraping, or by burning or applying heat, such as with a laser. These conventional layer-removal means do not provide reliably clean surfaces suitable for welding, and may also create undesirably airborne dust or smoke. Moreover, these require potentially dangerous equipment.

SUMMARY OF THE INVENTION

It is an object of the present invention to provide an improved method for making an aerosol dispensing container.

It is another object of the present invention to provide an aerosol container that can be manufactured inexpensively. A related, more specific object of the present invention is to provide an aerosol dispensing container which can be made of an inexpensive material, such as tinplated or tin-free steel, formed by welding along a seam, yet which provides good corrosion resistance.

A further object of the invention is to provide a method for making an aerosol container in which removal of the corrosion-resistant layer and specifically a laminate-stripping step is performed in a safe and clean manner.

These objects are achieved by means of the invention, wherein a method is provided that utilizes pressurized water jets to strip an anti-corrosion layer from a metal sheet. In one embodiment of the invention, the method for making an aerosol dispensing container uses a composite sheet having a metal layer and a corrosion-resistant layer on at least one surface of the metal layer. A water jet peeler or stripper is directed and applied to the surface of the composite sheet to remove a portion of the corrosion-resistant layer to expose the sites that are to be welded together. A generally rectangular blank is then formed from the composite sheet, such as by shearing or cutting so that the exposed areas, or portions thereof, are disposed generally along two opposite edges of the blank. It will be appreciated that the blank may also be stripped after it is cut from the composite sheet. The blank is then bent or otherwise shaped using conventional means into a tube or cylinder so that the exposed areas at opposite edges overlap each other. The overlapping edges of the blank are welded together at the exposed areas. Advantageously, the exposed areas formed by the water stripping step are clean areas which facilitate a good, reliable weld.

Additionally, an embodiment of the invention covers a method wherein the composite sheet has a laminated layer on the outside, such as for a label. The water jet stripping process of the invention could be applied to remove the exterior laminate from an exterior surface of the container body for aesthetic enhancement or to provide a weldable surface.

The water jet stripping process of the invention advantageously removes the plastic laminated or coated layer from a controlled area in an efficient manner, allowing a weld to be made, increasing production speed, and minimizing expenses. This is useful for stripping overlapping edges to be welded together.

These and other features and advantages are described in, and will be apparent from, the detailed description of the preferred embodiments, the drawings, and from the claims.

BRIEF DESCRIPTION OF THE DRAWINGS

FIG. 5 is an enlarged perspective schematic view of the blank of FIG. 4 indicating the direction in which the blank is rolled to form a body of a container.

FIG. 6A is an perspective schematic view of the blank of FIG. 5 shaped into a cylinder, whereby exposed areas of the blank overlap along a seam area prior to welding.

FIG. 6B is a perspective schematic view of the blank of FIG. 6A after welding.

DETAILED DESCRIPTION OF THE PREFERRED EMBODIMENTS

Figure 1:
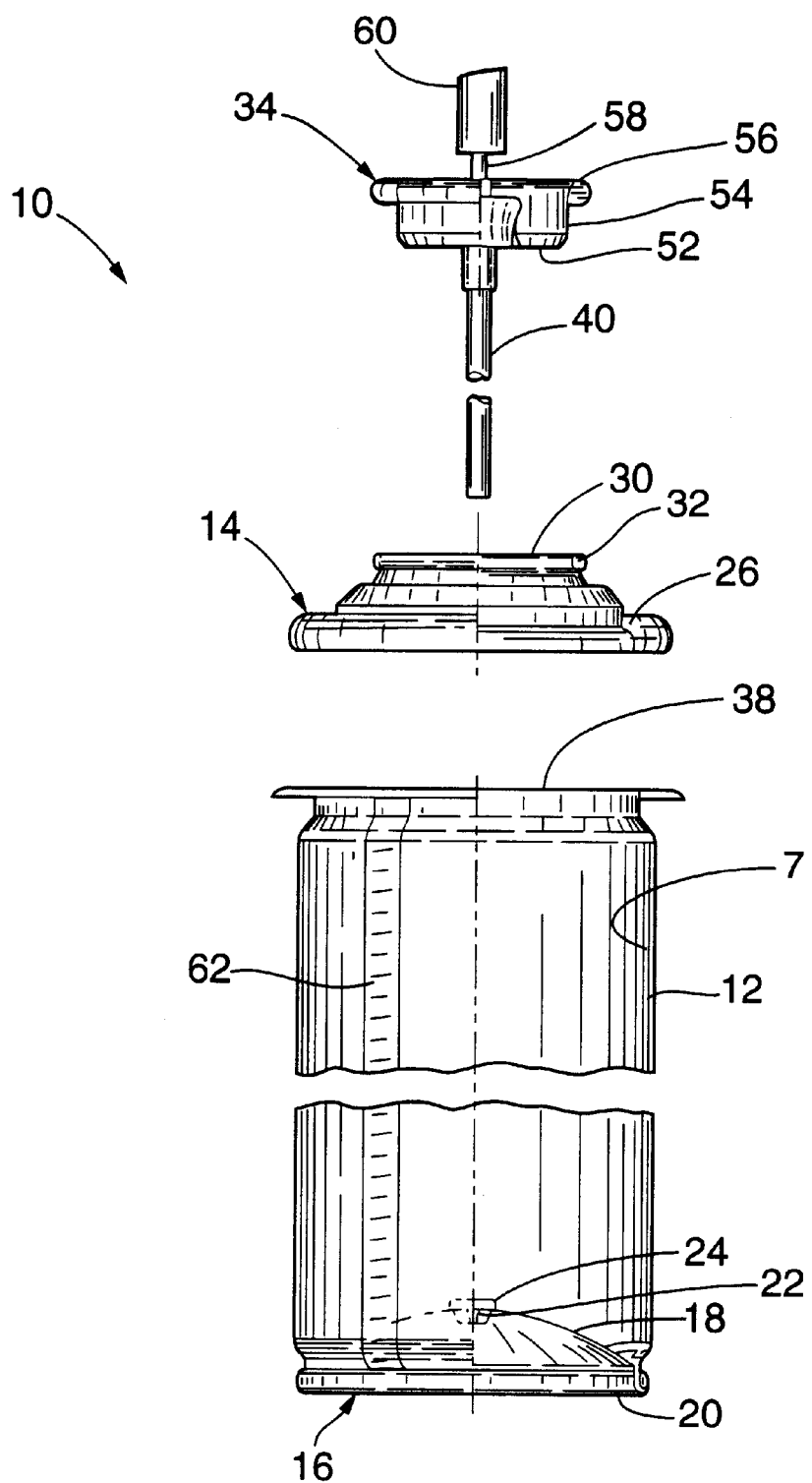
FIG. 1 is an exploded elevational view of an aerosol dispensing container made in accordance with the invention.

Now referring to the Figures, wherein like numerals designate like parts, in FIG. 1 there is shown a dispensing container 10 made in accordance with the present invention. The dispensing container 10 includes a preferably cylindrical and metallic tubular container body 12. The present invention relates to the manufacture of the body 12.

The body 12 has opposing top and bottom openings which are sealable by respective upper and lower closures 14, 16. The closures 14, 16 are secured to the body 12 by a conventional double seam. The lower closure 16 is preferably constructed from a metallic material and includes a generally upwardly dome-shaped or arcuate-shaped lower end panel 18. In one embodiment, the end panel 18 has a peripheral edge portion 20 and an aperture 22. A conventional grommet 24 or plug is disposed in the aperture 22 for selectively sealing the aperture 22. In another embodiment (not shown), the end panel 18 is a solid panel without the aperture or the grommet.

The upper closure 14 has a generally outward dome-like or conical configuration defining a base 26 which is secured to the body 12, preferably by a conventional double seam. The upper closure 14 also defines a valve opening 30. The peripheral edge of the valve opening 30 forms a smooth-surfaced, arcuate-shaped curl 32 which extends upwardly and outwardly from the center of the opening 30. The curl 32 interacts with a valve cup 34 to form an air-tight seal at the valve opening 30. The valve opening 30 communicates with an interior 38 of the container 10.

The interior 38 is adapted to receive, store, and selectively dispense products (not shown) such as shaving gels, creams, corrosive cleansers and the like. The interior 38 not only contains a product (not shown), but also a volume of pressurized propellant including, but not limited to, hydrocarbons, and other suitable compressed gas propellants. This propellant resides in an upper portion of the interior 38, pressing downwardly against the product to force the propellant upwardly through a tube 40.

The propellant may be introduced into the interior 38 by accurately seating the lower closure 18 upon a filling head (not shown) which includes a sealing gasket (not shown) and a conduit (not shown) in fluid communication with a propellant source (not shown). The propellant is introduced into the interior 38 through the aperture 22. After a predetermined quantity of propellant is introduced, the propellant source is terminated and the pressure of the propellant inside the container 10 exerts a downward force on the grommet 24 sealing the aperture 22.

The valve cup 34 has a base 52, a cylindrical wall 54, and an arcuate-shaped curl or flange 56. The dispensable product may be introduced into the interior 38 through either the aperture 22 with the filling head (not shown) equipped to deliver the product from a source (not shown), or a dispensable product may be introduced into the interior 38 through a dispensing member 58 after the valve cup 14 is attached to the container body 12. The dispensing member 58 is preferably valve actuated and, upon depressing a plunger 60, the product within the interior 38 is dispensed in a conventional manner under the influence of a propellant.

In order to assemble the container 10, the container body 12 is attached to the bottom end closure 16 by conventional seaming methods. The grommet 24 is preferably attached to the aperture 22 before the closure 16 and the container body 12 are attached, but may also be attached after such attachment.

The container body 12 has a vertical welded seam 62 joining together overlapping edges of the body 12 to form a cylindrical or tubular shape. Additionally, the body 12 has at least one surface comprising a laminated layer 74 which is made of a corrosion-resistant material. In the embodiment of FIG. 1, the corrosion-resistant layer 74 is disposed on a surface of the container body 12 facing the interior 38, but other embodiments could provide a laminated layer (not shown) on an outwardly-facing surface of the body 12 also.

Figure 2:
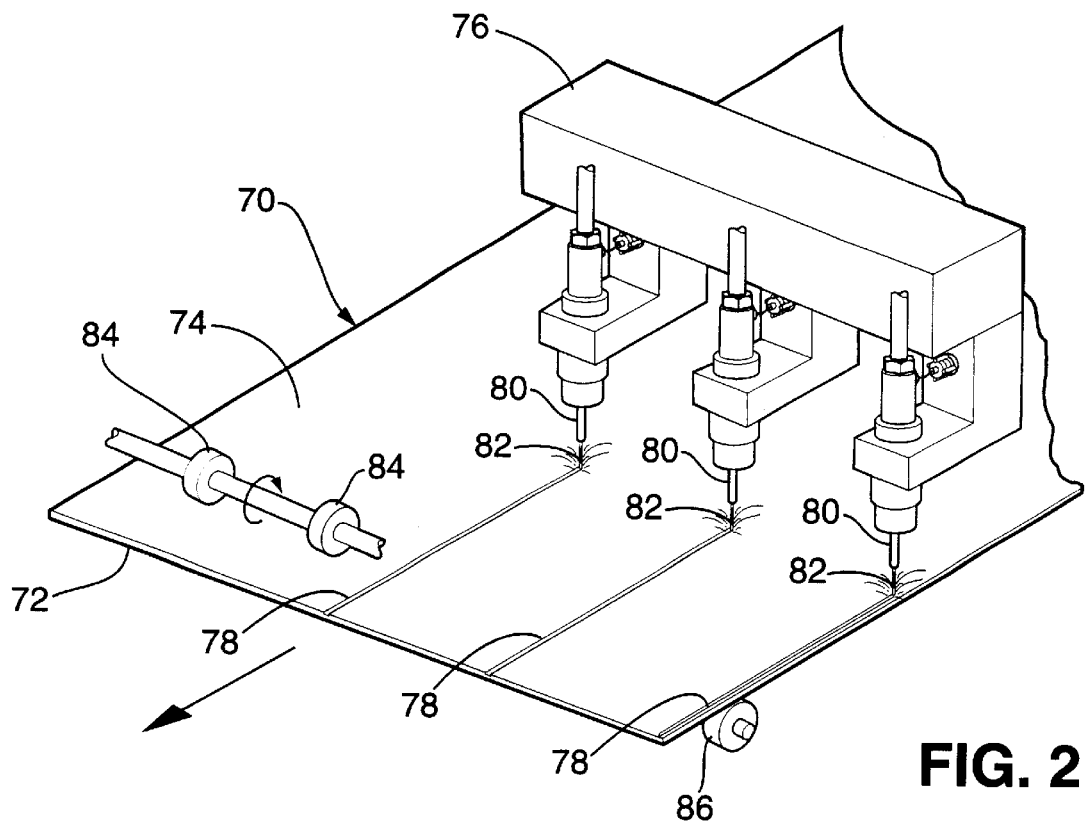
FIG. 2 is a schematic perspective view of a water jet stripping station illustrating a composite sheet comprising a metal layer laminated with a corrosion-resistant layer passing under a plurality of water jets which remove strips of the corrosion-resistant layer to expose selected areas of the metal layer.
Figure 3:
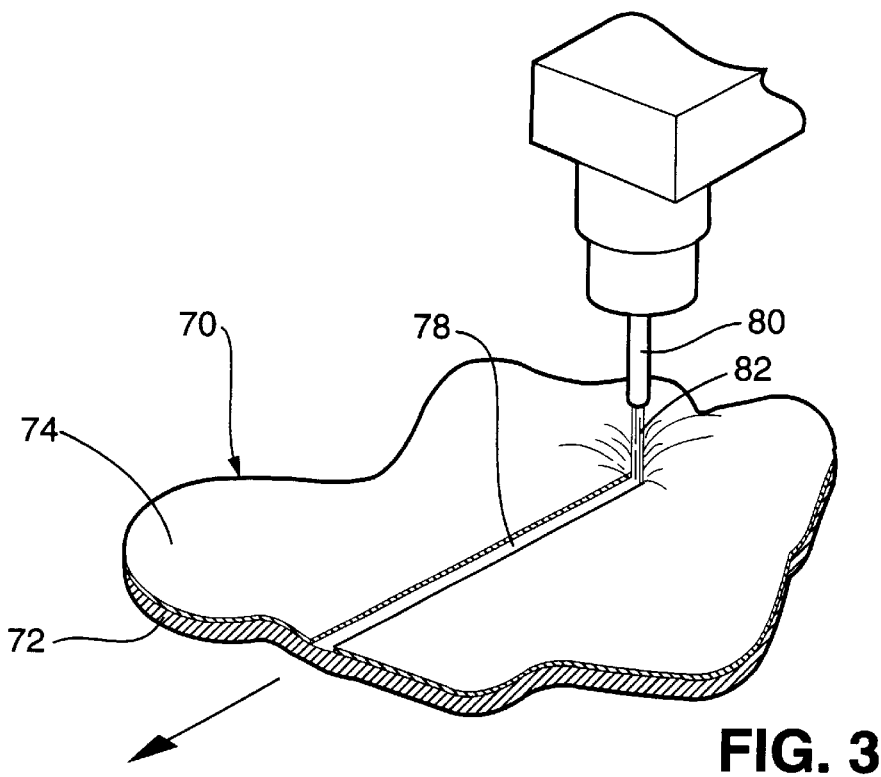
FIG. 3 is an enlarged fragmentary view of the composite sheet of FIG. 2 moving in the path of one of the water jets.

The body 12 of the container 10 (FIG. 1), according to the invention, is formed from a composite sheet 70 which, as shown in FIGS. 2 and 3 includes a metal layer 72 and a corrosion-resistant layer 74 disposed on at least one planar surface of the metal layer 74. In the composite sheet 70, the metal layer 72 is preferably made of tinplated or tin-free steel layer, and the corrosion-resistant layer 74 is made of corrosion-resistant material. In another embodiment, the composite sheet 70 could have a corrosion-resistant layer 74 on both sides (not shown) of the metal layer 72. In such a composite sheet which includes layers adhered to both sides of the metal layer, the layer intended to be disposed on the outside the container may serve, for example, as a label.

The corrosion-resistant layer 74 is preferably made of a thermoplastic, such as polyethylene terapthalate ("PET"), polypropylene, or polyamides. Other suitable materials are possible for making the corrosion-resistant layer 74 for various applications, such as various paints, waxes, lacquers, varnishes, etc. The material of the corrosion-resistant layer 74 is selected for compatibility with both the intended contents and the material selected for the metal layer 72. In particular, the corrosion-resistant layer 74 is selected from a material which resists corrosion from the product to be contained within the assembled container.

As discussed above in the Background section, welding a seam on a coated or laminated sheet has been problematic under some prior art manufacturing processes. The present invention provides an improved process for making an aerosol container, such as the container 10, which results in a reliable weld, minimizes manufacturing efforts, and minimizing expenses.

According to an aspect of the invention, a sheet-like section of the composite sheet 70 is processed by a water jet device 76 as generally illustrated in FIG. 2. The water jet device 76 is operable to remove a section of the corrosion-resistant layer 74 from the composite sheet 70, leaving exposed areas 78 of the tinplated metal sheet 72 below. Particularly, the water jet device 76 has one or more water jet nozzles 80, each delivering a high-pressure water jet 82.

The sheet 70 is moved under the nozzles 80 by an appropriate conveying means, such as upper and lower conveyor rollers 84 and 86, respectively, so that the jets 82 strip linear or strip-shaped portions of the corrosion-resistant layer 74 to form the exposed areas 78. The water jets 82 are of sufficient force to pulverize an area of the corrosion-resistant layer 74 as the composite sheet 70 is moved past the nozzles 80. The nozzles 80 are designed so that the water jets 82 have a size sufficient to effect the described stripping action at a desired width of the resulting exposed 78.

The water jet device 76 may be a standard apparatus, such as a device commercially available from Aquarese under the name Jet Edge. The water jets 82 have a high pressure, preferably about 2000 to 3000 bars. The water jet device 76 advantageously performs the striping action accurately and safely. Moreover, the use of water jets 82 is a clean process, because particulate matter from the pulverized laminate material is washed away instead of becoming airborne soil, as occurs with previous stripping methods.

Figure 4:
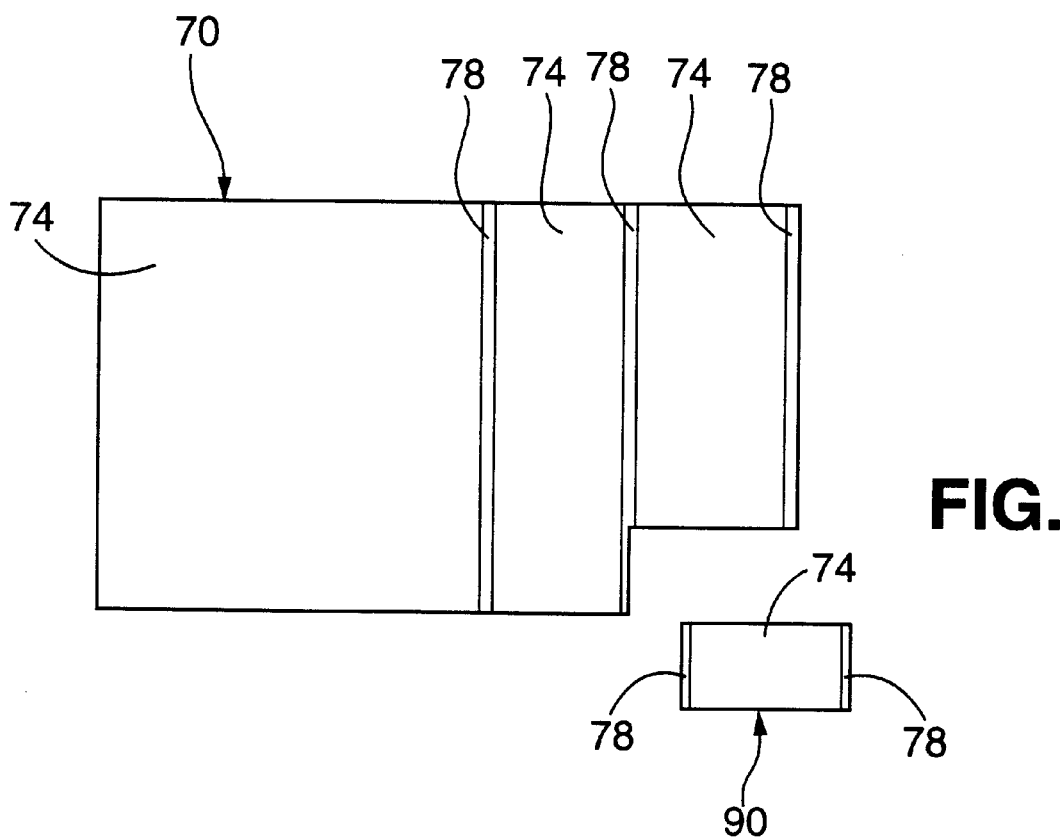
FIG. 4 is a plan view showing a blank cut from the composite sheet for making an individual container body.

After stripping the exposed areas of the composite sheet 70, the sheet 70 is segmented, as illustrated in FIG. 4, into individual can blanks 90, one of which is shown in greater detail in FIG. 5. For example, the sheet 70 can be cut with shears (not shown) or with a saw (not shown) into a plurality of blanks 90. Alternatively, the sheet can be either initially provided in the desired blank size or cut into the desired blank size prior to the water jet stripping step described above, and then the individual blanks 90 are passed under the water jets 82 to strip away portions of the corrosion-resistant layer. Either way, the blank 90 has two exposed areas 78 disposed along opposite edges.

It should be understood that when using a composite sheet (not shown) having a corrosion-resistant layer 74 on both sides of the metal layer 72, each side of the composite sheet must be processed with water jets 82 so to strip oppositely-positioned areas. This may be accomplished by turning over the composite sheet and passing it under the water jets a second time, or by using a water jet device (not shown) which has oppositely positioned jets that are directed both sides of the composite sheet. From such a composite sheet, the blank (not shown) has a corrosion-resistant layer on both sides, exposed areas 78 are formed oppositely on both sides of the blank. The corrosion resistant layer is removed from opposite sides in order to ensure proper welding.

Referring to FIG. 5, the blank 90 is bent as indicated by the arrows or is otherwise suitably formed into a tubular shape, such as the cylindrical shape illustrated in FIG. 6. Other tubular shapes could be possible, such as a rectangular tube (not shown), triangular tube (not shown), etc. In the tubular shape, the two opposite edges having the associated exposed areas 78, overlap. The bending is performed such that the corrosion-resistant layer 74 is positioned in a desired orientation on the resulting container body 12. For example, in the illustrated embodiment, the blank 90 is formed so that corrosion-resistant layer 74 is intended to be on an interior of the tubular or cylindrical shape.

Figure 7:
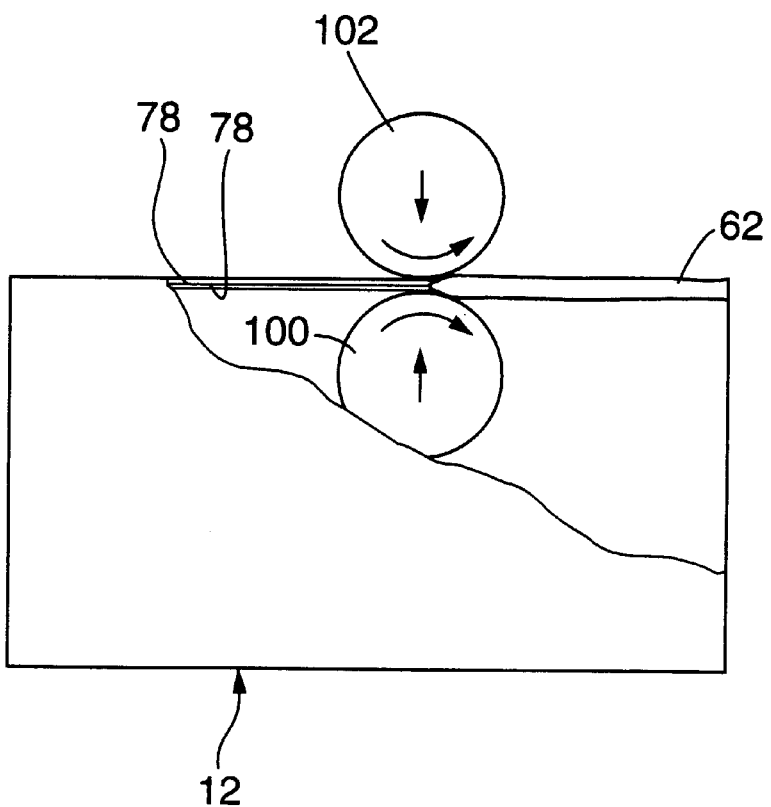
FIG. 7 is an perspective schematic view of the blank of FIG. 6 with a resistance welding apparatus welding the seam.

The tubular shaped blank 90 forming the body 12 is welded along the overlapping edges and associated exposed areas 78 in a standard manner, as illustrated schematically in FIG. 7. In order to hold the overlapping exposed areas together during welding, an inner roller 100 and outer roller 102 are provided at opposite sides of the body 12 to press toward each other with a pinching action. These rollers 100, 102 are the welding rolls that apply the electrical current to resistance-weld the exposed surfaces 78. Referring to FIG. 6B, the welding operation results in a fusing together of the previously overlapped exposed areas 78 (FIG. 6A) into the unitary welded seam 62.

After the seam 62 has been welded, the exposed areas 78 are covered with a corrosion-resistant material to prevent corrosion of the weld. For example, a powderized thermoplastic can be applied and cured, or a lacquer can be spray-applied.

While the invention is described herein in connection with certain preferred embodiments, there is no intent to limit it to those embodiments. On the contrary, it is recognized that various changes and modifications to the described embodiments will be apparent to those skilled in the art, and that such changes and modifications may be made without departing from the spirit and scope of the present invention. Accordingly, the intent is to cover all alternatives, modifications, and equivalents included within the spirit and scope of the invention as defined by the appended claims.

What is claimed is:

1. A method for making an aerosol dispensing container comprising:

providing composite sheet having a metal layer with a corrosion-resistant layer disposed on at least one side of the metal layer;

moving the sheet into the path of at least one high-pressure water jet;

removing a strip of corrosive-resistant layer material in the path of the water stream, leaving an exposed area;

segmenting the composite sheet into at least one blank having two opposite sides along which the exposed areas are disposed;

shaping the blank into a cylinder so that the opposite sides and respective exposed strips overlap each other and so that the corrosion-resistant layer faces interiorly of the cylinder; and welding the overlapped sides of the blank together forming a seam along the exposed areas.

2. A process for making an aerosol container comprising the steps of:

providing a sheet including metal layer and a corrosion-resistant layer;

stripping portions of the corrosion-resistant layer from the metal layer with at least one water jet so that the sheet has exposed areas where the corrosion-resistant layer is removed;

bending the sheet to overlap respective exposed areas; and welding the overlapping exposed areas.

3. The method according to claim 2, wherein the stripping step includes conveying the sheet generally linearly under the water jet so that the exposed areas are strip-shaped.

4. The method according to claim 2, wherein the corrosion-resistant layer is a thermoplastic.

5. The method according to claim 2, wherein the bending step includes bending the sheet into a tubular shape.

6. The method according to claim 5, wherein the corrosion-resistant layer faces an interior of the tube.

7. The method according to claim 5, wherein the tubular shape is cylindrical.

8. A method for making an aerosol dispensing container, the method comprising:

providing a composite sheet having a metal layer and a corrosion-resistant layer on at least one surface of the metal layer;

applying at least one water jet onto the laminated surface of the composite sheet to remove the corrosion-resistant layer from a corresponding portion of the laminated surface exposing at least two strip-shaped areas of the metal layer;

forming a generally rectangular blank from the composite sheet, at least portions of the exposed areas being disposed generally along two opposite edges of the blank;

overlapping the opposite edges having the exposed areas; and welding the overlapping edges of the blank together at said exposed areas.

9. The method according to claim 8, including applying a plurality of water jets to said composite sheet, the plurality of water jets simultaneously removing a plurality of corresponding portions of the corrosion-resistant layer.

10. The method according to claim 8, wherein the water jet has a pressure of about 2000–3000 bars.

11. The method according to claim 8, wherein the forming step includes segmenting the composite sheet into a plurality of blanks.

12. The method according to claim 8, wherein the metal layer is tinplated steel.

13. The method according to claim 8, wherein the corrosive-resistant layer is a thermoplastic.

14. The method according to claim 13, wherein the thermoplastic is selected from a group consisting of PET, polypropylene, and polyamides.

15. The method according to claim 8, wherein said overlapping step includes bending the blank into a generally cylindrical shape.

16. The method according to claim 15, wherein said overlapping step is such that said corrosion-resistant layer is positioned interiorly of said cylindrical shape.

17. The method according to claim 8, wherein the applying step includes:

moving said composite sheet in a planar manner; and directing said water jet generally perpendicularly toward the moving composite sheet.

18. The method according to claim 17, wherein said moving step includes moving said composite sheet horizontally.

19. The method according to claim 17, wherein said directing step includes directing said water jet generally downwardly.

20. The method according to claim 19 wherein the water jet ejects water a pressure between 2000 bars and 3000 bars.

* * * * *

UNITED STATES PATENT AND TRADEMARK OFFICE
CERTIFICATE OF CORRECTION

PATENT NO. : 6,328,197 B1
DATED : December 11, 2001
INVENTOR(S) : Gapihan

It is certified that error appears in the above-identified patent and that said Letters Patent is hereby corrected as shown below:

<u>Column 4,</u>
Line 36, after the number 74, insert the phrase -- and in intimate contact with the metal layer 74 --
Line 44, after the word outside, insert the word -- of --

<u>Columns 6-8,</u>
Beginning at Line 22, delete claims 1-20
Replace with following claims 1-20:
-- 1. A method for making an aerosol dispensing container the method comprising:
    providing a composite sheet having a metal layer and a corrosion-resistant layer on at least one surface of the metal layer, the corrosion-resistant layer being in intimate contact with the metal layer;
    applying at least one high-pressure water jet onto the laminated surface of the composite sheet to remove a portion of the corrosion-resistant layer from the at least one surface of the metal layer in a strip-shaped pattern to expose at least one strip-shaped area of the metal layer on the composite sheet; the water jet having a pressure of about 2000 bars or more;
    forming a generally rectangular blank from the composite sheet after said at least one strip-shaped area of the metal layer is exposed, at least portions exposed areas being disposed generally along two opposite edges of the blank;
    overlapping the opposite edges having the exposed areas; and
    welding the overlapping edges of the blank together at said exposed areas.
    2. The method according to claim 1, wherein said overlapping step includes bending the blank into a generally cylindrical shape.
    3. The method according to claim 2, wherein said overlapping step is such that said corrosion-resistant layer is positioned interiorly of said cylindrical shape.
    4. The method according to claim 1, wherein the applying step includes:
    moving said composite sheet in a planar manner relative to said water jet; and
    directing said water jet generally perpendicularly toward the moving composite sheet.
    5. The method according to claim 4, wherein said moving step includes moving said composite sheet horizontally.
    6. The method according to claim 4, wherein said directing step includes directing said water jet generally downwardly.
    7. The method according to claim 1, including applying a plurality of water jets to said composite sheet, the plurality of water jets simultaneously removing a plurality of corresponding strip-shaped portions of the corrosion-resistant layer.
    8. The method according to claim 1, wherein the water jet has a pressure of about 2000-3000 bars.
    9. The method according to claim 1, wherein the forming step includes segmenting the composite sheet into a plurality of blanks.
    10. The method according to claim 1, wherein the metal layer is tinplated steel.

UNITED STATES PATENT AND TRADEMARK OFFICE
CERTIFICATE OF CORRECTION

PATENT NO. : 6,328,197 B1
DATED : December 11, 2001
INVENTOR(S) : Gapihan

It is certified that error appears in the above-identified patent and that said Letters Patent is hereby corrected as shown below:

11. The method according to claim 1, wherein the corrosive-resistant layer is a thermoplastic.

12. The method according to claim 11, wherein the thermoplastic is selected from a group consisting of PET, polypropylene and polyamides.

13. A process for making an aerosol container comprising the steps of:
providing a sheet including metal layer and a corrosion-resistant layer on at least one surface of the metal layer, the corrosion-resistant layer being in intimate contact with the metal layer;
stripping portions of the corrosion-resistant layer from the surface of the metal layer with at least one water jet so that the sheet has exposed areas where the corrosion-resistant layer is removed, water being ejected from the water jet at a pressure greater than about 2000 bars;
bending the sheet to overlap respective exposed areas; and
welding the overlapping exposed areas.

14. The method according to claim 13, wherein the stripping step includes conveying the sheet generally linearly under the at least one water jet so that the exposed areas are strip-shaped.

15. The method according to claim 13, wherein the bending step includes bending the sheet into a tubular shape.

16. The method according to claim 15, wherein the corrosion-resistant layer faces interior of the tube.

17. The method according to claim 15, wherein the tubular shape is cylindrical.

18. The method according to claim 13, wherein the corrosion-resistant layer is a thermoplastic.

19. A method for making an aerosol dispensing container comprising:
providing a composite sheet having a metal layer with a corrosion-resistant layer disposed on at least one surface of the metal layer, the corrosion-resistant layer being in intimate contact with the metal layer;
moving the composite sheet into the path of at least one high-pressure water jet, the water jet ejecting water at a pressure greater than about 2000 bars;
removing a strip of corrosive-resistant layer material from the at least one surface of the metal layer in the path of the water stream, leaving an exposed, corrosive-resistant free strip-shaped area of the metal layer;
segmenting the composite sheet into at least one blank having two opposite sides along which the exposed areas are disposed;
shaping the blank into a cylinder so that the opposite sides and respective exposed areas overlap each other and so that the corrosion-resistant layer faces interiorly of the cylinder; and
welding the overlapped sides of the blank together forming a seam along the exposed areas.

UNITED STATES PATENT AND TRADEMARK OFFICE
CERTIFICATE OF CORRECTION

PATENT NO. : 6,328,197 B1
DATED : December 11, 2001
INVENTOR(S) : Gapihan

It is certified that error appears in the above-identified patent and that said Letters Patent is hereby corrected as shown below:

20. The method according to claim 19 wherein the water jet ejects water a pressure between 2000 bars and 3000 bars. --

Signed and Sealed this

Tenth Day of September, 2002

Attest:

Attesting Officer

JAMES E. ROGAN
*Director of the United States Patent and Trademark Office*